United States Patent
Le Saux et al.

(10) Patent No.: US 11,262,596 B2
(45) Date of Patent: Mar. 1, 2022

(54) METHOD OF DETERMINING A REFRACTIVE POWER VALUE CHARACTERISING AN OPHTHALMIC LENS AND CORRESPONDING ELECTRONIC DEVICE

(71) Applicant: Essilor International, Charenton-le-Pont (FR)

(72) Inventors: Gilles Le Saux, Charenton-le-Pont (FR); Stephane Boutinon, Charenton-le-Pont (FR); Cecile Pietri, Charenton-le-Pont (FR); Helene De Rossi, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 181 days.

(21) Appl. No.: 16/080,915

(22) PCT Filed: Mar. 4, 2016

(86) PCT No.: PCT/IB2016/000344
§ 371 (c)(1),
(2) Date: Aug. 29, 2018

(87) PCT Pub. No.: WO2017/149335
PCT Pub. Date: Sep. 8, 2017

(65) Prior Publication Data
US 2019/0072783 A1    Mar. 7, 2019

(51) Int. Cl.
*A61B 3/18* (2006.01)
*A61B 3/028* (2006.01)
(Continued)

(52) U.S. Cl.
CPC .............. *G02C 7/027* (2013.01); *A61B 3/028* (2013.01); *A61B 3/18* (2013.01); *G02C 7/061* (2013.01)

(58) Field of Classification Search
CPC ........ G02C 7/027; G02C 7/061; A61B 3/028; A61B 3/18
(Continued)

(56) References Cited

U.S. PATENT DOCUMENTS 6,048,064 A * 4/2000 Hosoi ................. A61B 3/0025
351/212
6,361,168 B1   3/2002 Fujieda
(Continued)

FOREIGN PATENT DOCUMENTS

CN           105190411 A     12/2015
DE   10 2008 035 247 A1     2/2010
(Continued)

OTHER PUBLICATIONS

International Search Report and Written Opinion dated Dec. 8, 2016, in PCT/IB2016/000344, filed Mar. 4, 2016.
(Continued)

*Primary Examiner* — James R Greece
(74) *Attorney, Agent, or Firm* — Oblon, McClelland, Maier & Neustadt, L.L.P.

(57) ABSTRACT

A method of determining a refractive power value characterising an ophthalmic lens for correction of an individual's eye ametropia includes: obtaining first data representative of a refraction value and second data representative of a position of the individual's head with respect to a refraction apparatus when the refraction value was determined; determining the refractive power value as a function of the first data and of a relative position, derived the second data, of the refraction apparatus with respect to a centre of rotation of the eye when the refraction value was determined. A corresponding electronic device is also proposed.

17 Claims, 2 Drawing Sheets

(51) Int. Cl.
*G02C 7/02* (2006.01)
*G02C 7/06* (2006.01)

(58) Field of Classification Search
USPC .................................................. 351/159.74
See application file for complete search history.

(56) References Cited

U.S. PATENT DOCUMENTS

| | | | |
|---|---|---|---|
| 7,118,215 B2 | 10/2006 | Qi et al. | |
| 8,303,114 B2* | 11/2012 | Berthezene | G02C 7/025 351/159.42 |
| 9,585,552 B2* | 3/2017 | Baranton | A61B 3/085 |
| 2004/0032565 A1 | 2/2004 | Yamakaji et al. | |
| 2010/0114540 A1* | 5/2010 | Shinohara | G02C 7/028 703/1 |
| 2010/0128220 A1 | 5/2010 | Chauveau | |
| 2010/0195045 A1 | 8/2010 | Nauche et al. | |
| 2011/0273664 A1* | 11/2011 | Guilloux | G02C 7/02 351/159.07 |
| 2012/0268713 A1* | 10/2012 | Guilloux | G02C 7/025 351/159.77 |
| 2012/0274902 A1* | 11/2012 | Baranton | A61B 3/113 351/206 |
| 2013/0314666 A1* | 11/2013 | Wietschorke | G02C 7/024 351/159.52 |
| 2013/0329186 A1* | 12/2013 | Contet | G02C 7/028 351/159.77 |
| 2015/0077704 A1 | 3/2015 | Carmon et al. | |
| 2015/0146168 A1 | 5/2015 | Divo et al. | |
| 2015/0309338 A1* | 10/2015 | Chauveau | A61B 3/1015 351/204 |
| 2015/0362747 A1 | 12/2015 | Kozu | |
| 2016/0011437 A1* | 1/2016 | Nishimura | G02C 7/061 351/204 |
| 2016/0274383 A1* | 9/2016 | Petignaud | G02C 7/027 |
| 2017/0109568 A1 | 4/2017 | Escalier | |

FOREIGN PATENT DOCUMENTS

| | | |
|---|---|---|
| FR | 2 914 173 A1 | 10/2008 |
| FR | 3 021 443 A1 | 11/2015 |
| JP | 6-181888 | 7/1994 |
| JP | 2001-95761 A | 4/2001 |
| JP | 2006-14903 | 1/2006 |
| JP | 2010-524011 | 7/2010 |
| JP | 2011-39552 A | 2/2011 |
| WO | WO 2007/017766 A2 | 2/2007 |
| WO | WO 2008/129168 A1 | 10/2008 |
| WO | WO 2010/119183 A1 | 10/2010 |
| WO | WO 2013/128439 A1 | 9/2013 |
| WO | WO 2014/006341 A1 | 1/2014 |

OTHER PUBLICATIONS

Combined Office Action and Search Report dated May 23, 2019 in Chinese Patent Application No. 201680083123.3 (with English translation citing document AO therein, 13 pages)

Japanese Office Action dated Dec. 3, 2019 in Patent Application No. 2018-546529 (with English translation), citing documents AO and AP therein, 6 pages.

Office Action dated Dec. 8, 2020 in Japan Patent Application No. 2020-13417 (English translation); 8 pgs.

* cited by examiner

Fig.3
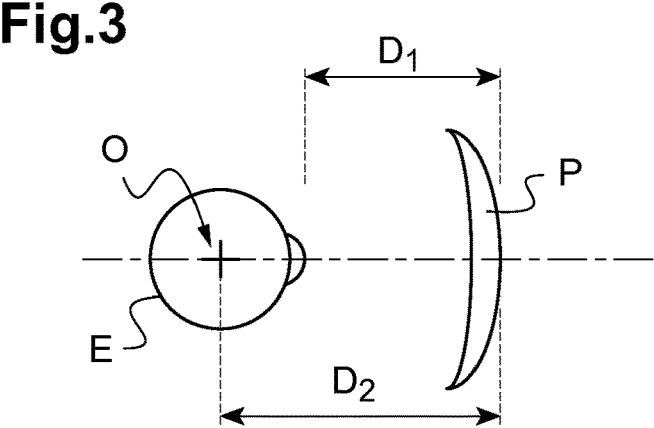
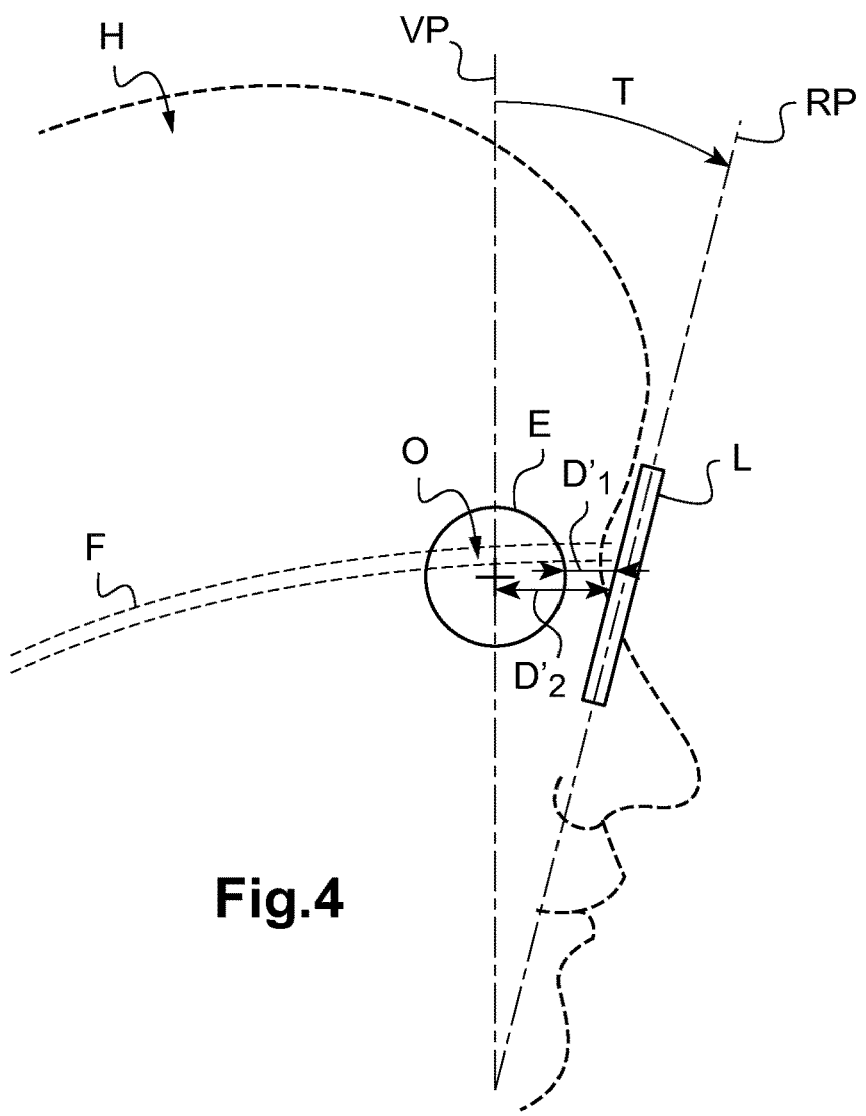
Fig.4

METHOD OF DETERMINING A REFRACTIVE POWER VALUE CHARACTERISING AN OPHTHALMIC LENS AND CORRESPONDING ELECTRONIC DEVICE

TECHNICAL FIELD OF THE INVENTION

The invention relates to the correction of ametropia.

More precisely the invention relates to a method of determining a refractive power value characterising an ophthalmic lens and to a corresponding electronic device.

BACKGROUND INFORMATION AND PRIOR ART

The necessary correction for compensating an individual's ametropia is generally determined by an optometrist or an ophthalmologist using a test known as "subjective refraction", during which the individual looks through a refraction apparatus adapted to generate a variable correction.

Such a refraction apparatus may be a phoropter or trial frames, for example.

The subjective refraction makes it possible to determine a refraction value (such as a spherical refractive power, a cylindrical refractive power or a cylinder axis) that an ophthalmic lens placed before the individual's eye should generate in order to compensate for the individual's ametropia.

The refraction value determined by the ophthalmologist or optometrist is communicated to the optician so that the latter can order an ophthalmic lens adapted to generate the desired refraction value before the individual's eye, taking into account in some instances the frame chosen by the individual.

SUMMARY OF THE INVENTION

In this context, the invention provides a method of determining a refractive power value characterising an ophthalmic lens for correction of an individual's eye ametropia, comprising the following steps:

obtaining first data representative of a refraction value and second data representative of a position of the individual's head with respect to a refraction apparatus when said refraction value was determined;

determining said refractive power value as a function of said first data and of a relative position, derived from said second data, of the refraction apparatus with respect to a centre of rotation of said eye when said refraction value was determined.

The position of the individual's head during the subjective refraction test is thus precisely taken into account to define the lens thanks to the use of the eye rotation centre, which improves the accuracy of the correction provided by the lens to the individual.

The method may have one or several of the following possible (non-limiting) features:

said relative position is determined by considering the position of the refraction apparatus when the refraction value was determined and the centre of rotation of said eye in a common three-dimensional frame of reference;

said value is determined such that a refractive power provided by the lens to the individual when said lens is worn before the individual's eye corresponds to a refractive power provided by the refraction apparatus to the individual when said refraction value was determined;

said value is also determined as a function of third data representative of a position, with respect to the individual's head, of a frame designed to carry said ophthalmic lens;

said third data includes a distance between the individual's eye and the ophthalmic lens when carried by the frame;

said third data includes a tilt angle and/or a face form angle of said frame;

said second data includes a distance between the individual's eye and the refraction apparatus;

said second data includes a yaw angle and/or a roll angle of the individual's head with respect to the refraction apparatus;

said second data includes three coordinates defining the location of the individual's head with respect to the refraction apparatus and three angles defining the orientation of the individual's head with respect to the refraction apparatus;

the method further comprises a step of designing an ophthalmic lens such that the designed ophthalmic lens has the determined refractive power value;

the method further comprises a step of manufacturing an ophthalmic lens having the determined refractive power value;

the method further comprises a step of selecting an ophthalmic lens having a refractive power value close to the determined value;

the step of determining the refractive power value comprises a sub-step of determining a modified refraction value based on said first data and said relative position, and the method then comprises a step of ordering an ophthalmic lens specifying the modified refraction value and data representative of a position, with respect to the individual's head, of a frame designed to carry said ophthalmic lens (the refractive power value being determined based on the modified refractive value and the data representative of the position of the frame);

the method comprises a step of ordering an ophthalmic lens specifying said first data, said relative position and data representative of a position, with respect to the individual's head, of a frame designed to carry said ophthalmic lens;

the method further comprises a step of ordering an ophthalmic lens specifying a lens power to be measured on a lensmeter as determined based on said first data, said relative position and data representative of a position, with respect to the individual's head, of a frame designed to carry said ophthalmic lens.

The invention also provides an electronic device comprising:

an input unit for obtaining first data representative of a refraction value and second data representative of a position of the individual's head with respect to a refraction apparatus when said refraction value was determined;

a processing unit adapted to determine a refractive power value characterising an ophthalmic lens for correction of an individual's eye ametropia as a function of said first data and of a relative position, derived from said second data, of the refraction apparatus with respect to a centre of rotation of said eye when said refraction value was determined.

BRIEF DESCRIPTION OF THE DRAWINGS

In the appended drawings:

FIG. 3 shows the positioning of the individual's eye with respect to a lens of a refraction apparatus when performing a subjective refraction;

FIG. 4 shows a frame chosen by the individual positioned on the individual's head.

DETAILED DESCRIPTION OF EXAMPLE(S)

Figure 1:
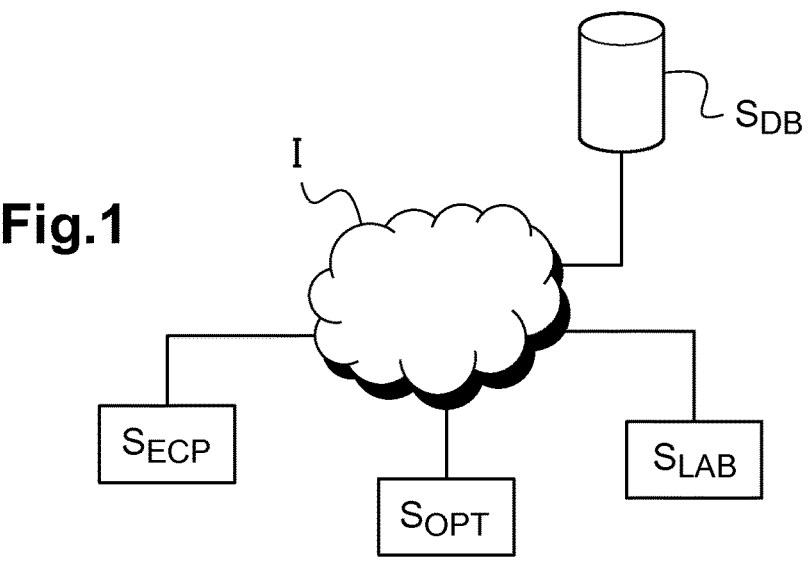
FIG. 1 shows an exemplary system in which the invention may be implemented.

The system shown in FIG. 1 includes an eye-care-professional computer system $S_{ECP}$, an optician computer system $S_{OPT}$, a manufacturing-lab computer system $S_{LAB}$ and a database computer system $S_{DB}$.

Each of these computer systems $S_{ECP}$, $S_{OPT}$, $S_{LAB}$, $S_{DB}$ includes a processor (for instance a microprocessor) and a storage device (such as a solid-state memory or a hard disk drive). In each computer system $S_{ECP}$, $S_{OPT}$, $S_{LAB}$, $S_{DB}$, the storage device stores computer program instructions that are executable by the processor such that the concerned computer system $S_{ECP}$, $S_{OPT}$, $S_{LAB}$, $S_{DB}$ may perform methods, including the methods described below for the concerned computer system, when these instructions are executed by the processor.

Each of these computer systems $S_{ECP}$, $S_{OPT}$, $S_{LAB}$, $S_{DB}$ also includes a communication module making it possible to connect the concerned computer system $S_{ECP}$, $S_{OPT}$, $S_{LAB}$, $S_{DB}$ to a communication network I, such as the Internet, and to exchange data with any other of the computer systems $S_{ECP}$, $S_{OPT}$, $S_{LAB}$, $S_{DB}$ via this communication network I. Data exchanges between the computer systems $S_{ECP}$, $S_{OPT}$, $S_{LAB}$, $S_{DB}$ may be encrypted by known means to ensure confidentiality of the exchanged data.

The eye-care-professional computer system $S_{ECP}$ is for instance located in the premises of an optometrist or an ophthalmologist. According to possible alternative embodiments mentioned below, an eye care professional may not have his/her own computer system; prescription data provided by such an eye care professional may be communicated to the optician in the form of a paper prescription.

In FIG. 1, the database computer system $S_{DB}$ is represented as a remote server, distinct for instance from the optician computer system $S_{OPT}$ and from the manufacturing-lab computer system $S_{LAB}$. In possible embodiments however, the database computer system $S_{DB}$ may be implemented jointly with the optician computer system $S_{OPT}$ or the manufacturing-lab computer system $S_{LAB}$, i.e. data stored in the database computer system $S_{DB}$ as described below may be stored in the optician computer system $S_{OPT}$ or in the database computer system $S_{DB}$.

Figure 2:
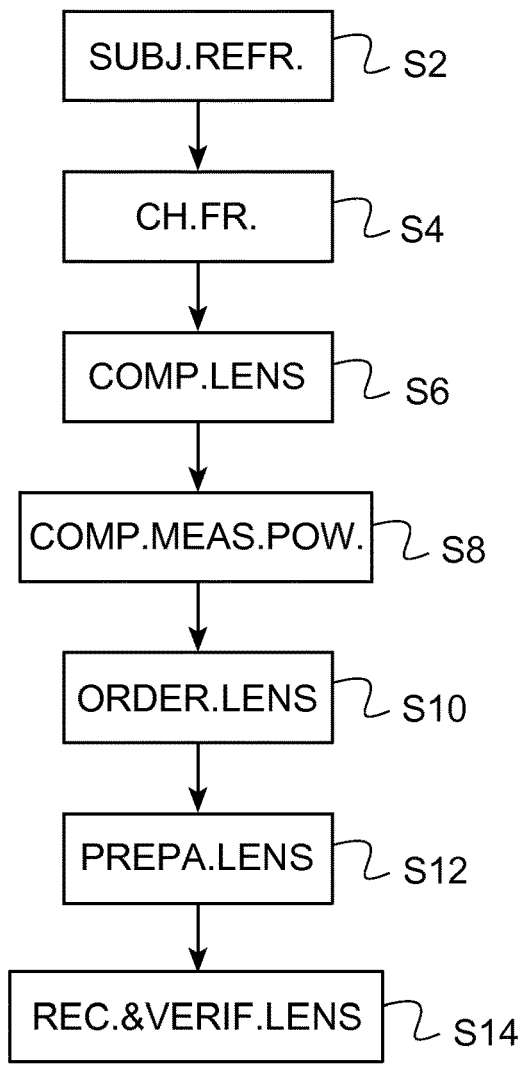
FIG. 2 shows a method for providing a lens to an individual, including steps in accordance with the invention.

FIG. 2 shows a method for providing a lens to an individual in order to compensate for the individual's ametropia.

This method starts at step S2 when an eye care professional, such as an ophthalmologist or an optometrist, performs a test of the individual's eye called "subjective refraction". An objective refraction, using an autorefractor or an aberrometer, may also be used as an alternative to the subjective refraction test.

During this test, the individual's eye is placed in front of the eyepiece of a refraction apparatus and the individual looks through the refraction apparatus.

The eye care professional may then modify the refractive power of the refraction apparatus in order to find a refractive power that provides the best correction for the individual.

Thus, for each eye of the individual, this test makes it possible to determine a refractive power to be provided to the individual, defined by the following prescription data: spherical refractive power S and/or cylindrical refractive power C and/or cylinder axis A. These refractive power values are generally known as "refraction values" and correspond to a desired correction of the individual's ametropia.

The subjective refraction test may be performed for a plurality of types of vision (e.g. distance vision and near vision), corresponding to a plurality of gaze direction, respectively.

The prescription data obtained thanks to the subjective refraction test may thus include, for each eye e and for each vision type t, a spherical refractive power $S_{e,t}$, a cylindrical refractive power $C_{e,t}$ and cylinder axis $A_{e,t}$.

In practice, prescription data for types of vision distinct from the distance vision (e.g. for the near vision) are generally presented by comparison with prescription data for the distance vision: for an eye e, prescription data includes a spherical refractive power $S_{e,d}$ and a cylindrical refractive power vector $\vec{C}_{e,d}$ for the distance vision (the cylindrical refractive power vector $\vec{C}_{e,d}$ defining the cylindrical refractive power $C_{e,d}$ and the cylinder axis $A_{e,d}$), the equivalent spherical power addition $EA_e$ for the other type of vision (e.g. for the near vision) and the vector variation $\vec{VC}_e$, for the other type of vision, of the cylindrical refractive power vector $\vec{C}_{e,d}$.

It is proposed here to take into account, as further explained below, the position of the individual's head with respect to the refraction apparatus during the subjective refraction test (for each eye and for each gaze direction). Parameters representing the position of the individual's head with respect to the refraction apparatus are thus measured during the subjective refraction test and recorded.

Thus, according to a possible embodiment, the distance $D_1$ between the cornea of the eye E under test and the optically active part P (e.g. a lens) of the refraction apparatus (see FIG. 3) may be determined and recorded.

In practice, such a determination is for instance performed by measuring a distance between the cornea and the eyepiece (e.g. using an image capturing device affixed to the refraction apparatus) and by adding thereto the known distance between the eyepiece and the optically active part.

According to other possible embodiments, other parameters defining the position of the individual's head with respect to the refraction apparatus may be considered, such as a distance $D_2$ between the centre O of rotation of the eye E under test and the optically active part P of refraction apparatus, and/or a yaw angle of the individual's head with respect to the refraction apparatus, and/or a roll angle of the individual's head with respect to the refraction apparatus.

In a possible embodiment, the position of the individual's head with respect to the refraction apparatus may be defined by three coordinates defining the location of the individual's head with respect to the refraction apparatus and three angles defining the orientation of the individual's head with respect to the refraction apparatus.

The parameters defining the position of the individual's head with respect to the refraction apparatus may be obtained for instance by use of a posture analysing device as described in the French patent application published as FR 3 021 443.

It may also be possible to use an average eye rotation centre position, in particular for the distance from the eye rotation centre to the refraction apparatus, for left eye and right eye. Using average eye rotation centre position for both eyes reduces complexity, without impairing accuracy for most refractive power values.

The distance between the centre of rotation of the left eye and the centre of rotation of the right eye may also be measured and recorded.

In order to define the position of the individual's head with respect to the refraction apparatus (e.g. by three coordinates and three angles as mentioned above), use can be made of a three-dimensional frame of reference R linked to the individual's head and defined as follows:

its origin $O_{REF}$ is the midpoint between the centre $O_L$ of rotation of the left eye and the centre $O_R$ of rotation of the right eye;

its first axis X passes through both centres of rotation $O_L$, $O_R$;

its second axis Y lies in the sagittal plane;

its third axis Z corresponds to the primary gaze direction.

The respective positions of the centres of rotation $O_L$, $O_R$ of the eyes may be determined for instance using the method described in the French patent application published as FR 2 914 173.

Hence, by using a measurement apparatus having a fixed position with respect to the refraction apparatus and adapted to determine the respective positions of the centres of rotation and thus the position of the frame of reference R, it is possible to determine the position of the refraction apparatus (represented e.g. by three coordinates and three angles) in the frame of reference R, i.e. to obtain parameters defining the position of the individual's head with respect to the refraction apparatus.

According to a possible embodiment, the actual gaze direction of each eye during the subjective refraction test may be measured and recorded for each type of vision (distance vision, intermediate vision and near vision, for example).

The various data obtained during the subjective refraction as explained above (i.e. in particular, for each eye and for each gaze direction considered, data defining the refractive power to be provided to the individual and data defining the position of the individual's head with respect to the refraction apparatus) may then be entered in the eye-care-professional computer system $S_{ECP}$ and transmitted to the database computer system $S_{DB}$ where it is stored, e.g. in association with an identifier of the concerned individual (possibly in the form of a matrix barcode).

As already noted, in possible embodiments, these data may however be written by the eye care professional on a paper prescription to be later given to the optician by the individual.

The method of FIG. 2 continues at step S4, where the individual chooses a frame at an optician's. This frame is meant to carry a pair of ophthalmic lenses, each lens being designed to provide the individual with the refractive power mentioned above, as explained below.

When worn by the individual as shown in FIG. 4, the frame F has a position with respect to the individual's head H, which position may be defined by several parameters, such as a distance between one of the individual's eye E and the corresponding lens L carried by the frame F, a face form angle and a tilt angle T.

The distance between the eye E and the lens L considered may be for instance the distance $D'_2$ between the centre O of rotation of the eye E and the lens L, or, as a variation, the distance $D'_1$ between the cornea and the lens L.

The face form angle is the angle between a mean vertical plane of a rim of the frame and a vertical plane that is perpendicular to the sagittal plane of the individual's head.

The tilt angle T is the angle between a plane RP containing the rim and a vertical plane VP (containing for instance the centre O of rotation of the corresponding eye).

The values of such parameters for the frame chosen by the individual may be measured during step S4 using for instance a measurement device as described in the PCT application published as WO 2008/129 168.

The measured values can then be stored in the optician computer system $S_{OPT}$ (either by being entered on the optician computer system $S_{OPT}$ or by being automatically transferred thereto by the measurement device), and possibly be transmitted to the database computer system $S_{DB}$ for remote storage in association with the individual's identifier.

In the embodiments where data obtained in the subjective refraction step S2 are communicated to the optician using a paper prescription, these data may also be entered in the optician computer system $S_{OPT}$ at this stage using an input module (such as a user interface) and possibly transmitted to the database computer system $S_{DB}$ for remote storage.

According to a possible variation, parameters relating to the position of the frame with respect to the individual's head can be evaluated, for instance by simulating the positioning of the frame on the individual's head and/or based on predetermined values associated with the chosen frame.

Then, in step S6, the optician selects a type of lens (for instance among a list of possible types of lens) and launches a first tool (here a software tool executed on the optician computer system $S_{OPT}$) designed to determine (e.g. compute) parameters characterising each of the ophthalmic lenses to be mounted in the chosen frame in order to obtain the refractive power needed to compensate for the individual's ametropia. In some embodiments (wherein these parameters are not used when ordering the lens), this first tool can be implemented during step S12 described below.

The type of lens (e.g. spherical, bifocal, progressive) is chosen by the optician depending on the prescription and on the individual's preferences.

Precisely, for each eye of the individual, the first tool is designed to compute these parameters characterising the lens based on:

refractive power values obtained (possibly for a plurality of gaze direction) during the subjective refraction test, parameters representing the relative position of the refraction apparatus with respect to the eye rotation centre O during the subjective refraction test (possibly with specific values for each of the gaze direction tested), parameters representing the position of the frame with respect to the individual's head, and characteristics of the selected type of lens (such as material and/or thickness and/or lens shape such as lens front or back curvature and/or optical design of the lens).

Refractive power values may for instance be retrieved from the database computer system $S_{DB}$ (based e.g. on the individual's identifier mentioned above).

Parameters representing the relative position of the refraction apparatus with respect to the eye rotation centre O during the sujective refraction test may also be retrieved from the database computer system $S_{DB}$ when measurements of the position of the individual's head with respect to the refraction apparatus made during step S2 take into account the position of the eye rotation centre O (such as the distance $D_2$ mentioned above between the centre O of rotation of the eye E under test and the optically active part P of refraction apparatus).

However, when measurements of the position of the individual's head with respect to the refraction apparatus made during step S2 (and obtainable from the database computer system $S_{DB}$) do not take into account the position of the eye rotation centre O (e.g. here when measuring the distance $D_1$ between the cornea of the eye E under test and the optically active part P of the refraction apparatus), a measurement of the (e.g. three-dimensional) position of the eye rotation centre O is made by the optician in step S4 so as to be able to locate this eye rotation centre O with respect to the individual's head (in particular with respect to the part of the head, here the cornea, used as reference to define the position of the individual's head with respect to the refraction apparatus in step S2) and thus to obtain the position of the eye rotation centre O and the position of the refraction apparatus during the subjective refraction in the same three-dimensional frame of reference, e.g. the frame of reference R mentioned above.

The first tool is designed to determine the parameters characterising the lens in such a manner that, for each gaze direction considered, the refractive power provided by the lens when mounted in the frame (supposedly positioned on the individual's head) is identical to the refractive power provided by the refraction apparatus during the subjective refraction test (this refractive power being determined from the refraction values, represented by first data, and the parameters representing the relative position of the refraction apparatus with respect to the eye rotation centre O during the subjective refraction test).

The refractive power provided by the refraction apparatus may be determined from the first data representative of refraction values and from the relative position of the refraction apparatus with respect to the eye rotation centre in the following way:

If the equivalent spherical power (refraction value) represented by the first data is noted Sa, the equivalent spherical power Sam of the refractive power provided by the refraction apparatus can be determined as follows:

$$1/Sam = 1/Sa - D_2 \qquad (1).$$

If the equivalent spherical power of the refractive power provided by the lens is noted Sl, the equivalent spherical power Slm of the refractive power provided by the lens taking account of the parameters representing the position of the frame with respect to the individual's head can be determined as follows:

$$1/Slm = 1/Sl - D_2' \qquad (2).$$

If the distance $D_2'$ is not determined, a standard value, for example $D_2' = 27$ mm, can be used instead.

Cylindrical refractive power can be handled in a similar manner by applying the above formulae to the minimum and maximum refractive power.

As explained above, the lens is thus designed so that Slm=Sam for a spherical lens or, when the lens has cylinder, such that minimum and maximum power are equal for the refractive power provided by the lens and the refractive power provided by the refraction apparatus using formulae (1) and (2).

It should be noted that the determination of the refractive power provided by the refraction apparatus may be done in previous step, for example step S2 mentioned above. In this case, the optometrist or ophthalmologist conducting the refraction in step S2 may transmit this refractive power to the optician, and it is not necessary in this case to transmit to the optician the relative position of the refraction apparatus with respect to the eye rotation centre.

This last example corresponds to the case when the first data mentioned above are representative of power provided by the refraction apparatus at the eyepiece position.

The refractive power may also include high order optical aberration (coma, trefoil, etc.), when the refraction instrument is for example an aberrometer. In this case, it is proposed, using for example ray tracing, to calculate the propagation of the initial optical wavefront from the eyepiece of the aberrometer to the position of the eye rotation centre. This particularly applies when the wavefront measured by the aberrometer is determined at the eyepiece position. The initial wavefront can be a sum of Zernicke polynoms, and the propagated wavefront is then also a sum of Zernicke polynoms having coefficients different form the initial wavefront.

In addition, the equivalent spherical power of the refractive power may also take account of the real distance of the target used when performing the subjective refraction test. For example, if the far vision distance used is DtargetFV, the equivalent spherical power S' for far vision may be modified in the following way: $S'' = S' - 1/DtargetFV$. If the equivalent spherical EAe' is determined at a near distance DtargetNV different from a reference near vision distance DtargetNVref, the modification can be as follows: $EAe'' = EAe' - (1/DtargetNV - 1/DtargetNVref)$.

The parameters characterising the lens may be determined in practice using a ray tracing method or a method such as described in the PCT application published under WO 2007/017 766.

The computations just mentioned may be performed by the optician computer system $S_{OPT}$ (where the software tool is executed), or may be performed (totally or in part) by a (dedicated) remote computer system (connected to the optician computer system $S_{OPT}$).

According to a possible variation, parameters characterising the lens are pre-computed for (a great number of) possible values of refractive power obtained during the subjective refraction test, for possible values of parameters representing the position of the individual's head with respect to the refraction apparatus during the subjective refraction test, for possible values of parameters representing the position of the frame with respect to the individual's head, and for possible characteristics of the possible types of lenses. Pre-computed values are stored in look-up tables in the optician computer system $S_{OPT}$ or in the database computer system $S_{DB}$.

In such embodiments, step S6 includes reading the parameters characterising the lens stored in the look-up tables just mentioned in association with:

refractive power values obtained during the subjective refraction test (step S2), parameters representing the relative position of the refraction apparatus with respect to the eye rotation centre O during the subjective refraction test (step S2), parameters representing the position of the frame with respect to the individual's head (measured in step S4), and characteristics of the type of lens selected in step S6.

The optician can then launch at step S8 a second tool (here a software tool executed by the optician computer system $S_{OPT}$) designed to determine the power to be measured on a lensmeter (or focimeter) for a lens as defined by the parameters determined in step S6 (this determination being performed for both lenses to be mounted on the selected frame).

These parameters include for instance one or several of the following parameters: a distance between the lens and the wearer's eye and/or an orientation of the lens with respect to the wearer's eye (both derived from the parameters representing the position of the frame with respect to the individual's head), a refractive power of the lens, a shape and/or geometry of at least part of the lens, a refraction index of a material forming the lens, an optical design.

The determination of the power to be measured on a lensmeter can be done for instance in practice by simulating a bundle of parallel light rays of small diameter (e.g. 4 mm) entering a front face of the lens (the rear face of the lens being perpendicular to the light rays where crossed by the light rays), by determining the focus based on the wave front of the light rays at the rear face and by determining the power to be measured based on the distance between the rear face and the determined focus. In particular, this simulation can be done using determined parameters characterising the lens if available from the first tool mentioned above.

According to a possible variation, the power to be measured on a lensmeter may be determined by reading the relevant record in a look-up table storing predetermined power values each associated with a given set of values of the parameters determined in step S6. Each power value in the look-up table may be obtained previously either by simulating the effect of a lens defined by the concerned set of parameters or by measuring on a lensmeter the power of a lens designed as defined by the concerned set of parameters.

The determined power (in dioptres) may be rounded to the nearest quarter dioptre (e.g. 1.3 D is rounded to 1.25 D), or eighth dioptre (e.g. 1.15 D is rounded to 1.125 D).

The optician then orders the ophthalmic lenses at step S10 specifying, for each ophthalmic lens, the power determined in step S8 (power to be measured on a lensmeter).

The ophthalmic lenses are for instance ordered electronically by sending an electronic order from the optician computer system $S_{OPT}$ to the manufacturing-lab computer system $S_{LAB}$.

The order may also include complementary data, such as the type of lens selected in step S6 and/or the parameter(s) characterising the lens as determined in step S6. These complementary data may include parameters representing the position of the frame with respect to the individual's head, as determined in step S4, particularly when the lens is a progressive lens.

According to a possible alternative embodiment, the order to the manufacturing lab may include, for each ophthalmic lens:

the type of the concerned lens;

refractive power values obtained (possibly for a plurality of gaze direction) during the subjective refraction test, parameters representing the relative position of the refraction apparatus with respect to the eye rotation centre O during the subjective refraction test (possibly with specific values for each of the gaze direction tested), and parameters representing the position of the frame with respect to the individual's head.

In such an embodiment, each lens will then be designed in the manufacturing lab in such a manner that, for each gaze direction considered, the refractive power provided by the lens when mounted in the frame (supposedly positioned on the individual's head) is identical to the refractive power provided by the refraction apparatus during the subjective refraction test (this refractive power being determined from the refractive power values and the parameters representing the position of the individual's head with respect to the refraction apparatus during the subjective refraction test).

According to yet another possible embodiment, the order may include:

the type of the concerned lens;

refractive power values obtained during the subjective refraction test and modified to take into account the relative position of the refraction apparatus with respect to the eye rotation centre O, and parameters representing the position of the frame with respect to the individual's head.

In this embodiment, the optician computer system $S_{OPT}$ is adapted to compute the modified refractive power values based on the refractive values obtained during the subjective refraction test and on the parameters representing the relative position of the refraction apparatus with respect to the eye rotation centre O during the subjective refraction test. (These refractive values and these parameters may be retrieved in the database computer system $S_{DB}$, or computed based on data retrieved in the database computer system $S_{DB}$ and based on further information such as a position of the eye rotation centre O in the frame of reference R, as explained above, or even read by the optician on a paper prescription.)

The modified refractive power values correspond to values that would have been obtained for a predetermined (standard) position of the individual's head with respect to the refraction apparatus, for example for a standard distance $D_2$std=27 mm. As an example, if the distance $D_2$ differs from $D_2$std, the modified refractive power values may be determined the following way:

$1/Smod=1/Sa-(D_2-D_2std)$

Sa being the equivalent spherical power (represented by first data), and Smod being the equivalent spherical power of the modified refractive power.

This can be generalised to cylindrical refractive power by applying the formula to the minimum and maximum refractive power.

The ordered lenses are then prepared by the manufacturing lab at step S12.

In some embodiments, this merely amounts to collect, in a stock of prefabricated lens, a lens having a refractive power (as measured on a lensmeter) equal to the power specified in the order (in particular when this power is rounded to the nearest quarter or eighth dioptre as proposed above), or a lens which refractive power is the nearest to the power specified in the order.

In other embodiments (e.g. for progressive lenses), this involves designing a lens that matches the constraints defined in the order and manufacturing the designed lens.

For instance, in the case of a progressive lens, the order includes the above-mentioned refractive power to be measured on a lensmeter and an addition to be measured on the lensmeter (defining the lens for a gaze direction corresponding to near vision).

The rear face of the lens (and/or the front face of the lens) can thus be designed (for instance by simulation using ray tracing) such that the refractive power provided by this face (as measured on a lensmeter) in a first region corresponding to distance vision equals then refractive power mentioned in the order, and such that the refractive power provided by this face (as measured on a lensmeter) in a second region corresponding to near vision equals the refractive power defined by the addition mentioned in the order.

The prepared lenses are packed and sent to the optician.

When the order specifies the refractive power to be measured on a lensmeter, it is proposed here that the pack carrying a lens only indicates the refractive power to be measured for this lens on a lensmeter.

The optician receives the lenses at step S14, with the indication of the refractive power to be measured on a lensmeter for each lens.

The optician can thus place each lens on his/her own lensmeter and verify that the refractive power of the concerned lens measured by the lensmeter corresponds to the value indicated on the pack (and thus to the value specified in the order).

As the only refractive power value used when ordering and when verifying is the value to be measured on the lensmeter, there is no risk of mixing with another refractive power value characterising the lens.

According to a possible variation, the refractive power value may also be determined using additional parameters, for example using the known optical combination of the lenses used in the refractive apparatus. It is indeed possible, using for example ray tracing calculation, to determine the exact refractive power provided by the refractive apparatus.

Ray tracing may use simulated bundle of light rays, starting from a source situated at a position corresponding to the position of the visual stimulus when the refraction is performed, then the bundle of light rays is propagated through the different optical components (lens, mirror, etc.) of the refraction apparatus, having the optical characteristic and position used during refraction, and then propagated until the eye rotation centre.

This allows an higher accuracy for the refraction power value measurement, in particular when using trial frames or phoropter for which the sum of the power of the lenses used to make the refraction is not exactly equal to the power provided by this combination.

The invention claimed is:

1. A method of determining a refractive power value characterizing an ophthalmic lens for correction of an eye ametropia of an individual, comprising:
    obtaining first data representative of a refraction value and second data representative of a position of a head of the individual with respect to a refraction apparatus when said refraction value was determined, said refraction apparatus including an optically active part so that said refraction apparatus provides a refractive power to the individual; and
    determining said refractive power value as a function of said first data and of a relative position, derived from said second data, of the refraction apparatus with respect to a center of rotation of an eye of the in when said refraction value was determined, said value being determined such that a refractive power provided by the lens to the individual when said lens is worn before the eve of the individual corresponds to the refractive power provided by the refraction apparatus to the individual when said refraction value was determined.

2. The method according to claim 1, wherein said relative position is determined by considering the position of the refraction apparatus when the refraction value was determined and the center of rotation in a common three-dimensional frame of reference.

3. The method according to claim 1, wherein said refractive power value is also determined as a function of third data representative of a position, with respect to the head of the individual, of a frame designed to carry said ophthalmic lens.

4. The method according to claim 3, wherein said third data includes a distance between the eye of the individual and the ophthalmic lens when carried by the frame.

5. The method according to claim 3, wherein said third data includes a tilt angle of said frame.

6. The method according to claim 3, wherein said third data includes a face form angle of said frame.

7. The method according to claim 1, wherein said second data includes a distance between the eye of the individual and the refraction apparatus.

8. The method according to claim 1, wherein said second data includes a yaw angle of the head of the individual with respect to the refraction apparatus.

9. The method according to claim 1, wherein said second data includes roll angle of the head of the individual with respect to the refraction apparatus.

10. The method according to claim 1, wherein said second data includes three coordinates defining a location of the head of the individual with respect to the refraction apparatus and three angles defining an orientation of the head of the individual with respect to the refraction apparatus.

11. The method according to claim 1, further comprising designing an ophthalmic lens such that the designed ophthalmic. lens has the determined refractive power value.

12. The method according to claim 1, further comprising manufacturing an ophthalmic lens having the determined refractive power value.

13. The method according to claim 1, further comprising selecting an ophthalmic lens having a refractive power value close to the determined refractive power value.

14. The method according to claim 1, wherein the determining the refractive power value further comprises determining a modified refraction value based on said first data and said relative position; and
    wherein the method further comprises ordering an ophthalmic lens specifying the modified refraction value and data representative of a position, with respect to the head of the individual, of a frame designed to carry said ophthalmic lens.

15. The method according to claim 1, further comprising ordering an ophthalmic lens specifying said first data, said relative position and data representative of a position, with respect to the head of the individual, of a frame designed to carry said ophthalmic lens.

16. The method according to claim 1, further comprising ordering an ophthalmic lens specifying a lens power to be measured on a lensmeter as determined based on said first data, said relative position and data representative of a position, with respect to the head of the individual, of a frame designed to carry said ophthalmic lens.

17. An electronic device comprising:
    input circuitry configured to obtain first data representative of a refraction value and second data representative of a position of a head of an individual with respect to a refraction apparatus when said refraction value was determined, said refraction apparatus including an optically active part so that said refraction apparatus provides a refractive power to the individual; and
    processing configured to determine a refractive power value characterizing an ophthalmic lens far correction of an eye ametropia of the individual as a function of said first data and of a relative position, derived from said second data, of the refraction apparatus with respect to a center of rotation of an eye of the individual when said refraction value was determined, said value being determined such that a refractive power provided by the lens to the individual when said lens is worn before the eye of the individual corresponds to the refractive power provided by the refraction apparatus to the individual when said refraction value was determined.

* * * * *